United States Patent [19]

Stegmann

[11] Patent Number: 5,047,591
[45] Date of Patent: Sep. 10, 1991

[54] SINGLE-STAGE PROCESS FOR PRODUCING BIS-(AMINO-NITROPHENYL)-METHANE

[75] Inventor: Werner Stegmann, Liestal, Switzerland

[73] Assignee: Ciba-Geigy Corporation, Ardsley, N.Y.

[21] Appl. No.: 241,828

[22] Filed: Sep. 6, 1988

Related U.S. Application Data

[63] Continuation of Ser. No. 142,241, Jan. 4, 1988, abandoned, which is a continuation of Ser. No. 20,243, Feb. 27, 1987, abandoned, which is a continuation of Ser. No. 789,253, Oct. 18, 1985, abandoned.

[30] Foreign Application Priority Data

Oct. 30, 1984 [CH] Switzerland ............... 5181/84

[51] Int. Cl.$^5$ ..................................... C07C 209/78
[52] U.S. Cl. ................. 564/331; 564/330; 564/332; 564/334; 564/335
[58] Field of Search ............ 564/330, 335, 332, 331, 564/334

[56] References Cited

U.S. PATENT DOCUMENTS

| 2,818,433 | 12/1957 | Erickson | 564/331 X |
| 3,097,191 | 7/1963 | France et al. | 564/333 X |
| 3,274,247 | 9/1966 | Repper | 564/331 X |
| 3,358,025 | 12/1967 | Foster et al. | 564/331 |
| 3,367,969 | 2/1968 | Perkins | 564/333 |
| 3,429,856 | 2/1969 | Hoeschele | 564/331 |
| 3,476,806 | 11/1969 | Wolf | 564/333 |

FOREIGN PATENT DOCUMENTS

| 714092 | 7/1965 | Canada | 564/331 |
| 0099516 | 2/1984 | European Pat. Off. | |
| 1107440 | 3/1968 | United Kingdom | |
| 1167950 | 10/1969 | United Kingdom | 564/331 |
| 1228495 | 4/1971 | United Kingdom | |
| 1292078 | 10/1972 | United Kingdom | |

Primary Examiner—Richard L. Raymond
Attorney, Agent, or Firm—Harry Falber

[57] ABSTRACT

Bis-(amino-nitrophenyl)-methane can be produced in one stage with an approximately quantitative yield by condensing o-nitraniline and formaldehyde in water at a temperature of between 20° and 40° C. in the presence of sulfuric acid, and subsequently rearranging the formed methylene-bis-(o-nitraniline) by treatment of the reaction mixture at a temperature of between 90° and 100° C.

2 Claims, No Drawings

SINGLE-STAGE PROCESS FOR PRODUCING BIS-(AMINO-NITROPHENYL)-METHANE

This application is a continuation of application Ser. No. 142,241, filed Jan. 4, 1988, now abandoned, which is a continuation, of application Ser. No. 020,243, filed Feb. 27, 1987, now abandoned, which is a continuation, of application Ser. No. 789,253, filed Oct. 18, 1985, now abandoned.

The present invention relates to a process for producing bis-(amino-nitrophenyl)-methane by condensation of nitraniline with formaldehyde, and subsequent rearrangement of the resulting methylene-bis-nitraniline in one stage in the presence of aqueous sulfuric acid.

A production method for bis-(4-amino-3-nitrophenyl)methane in two stages is known from the FR patent specification No. 1,462,569. In the first stage is performed the condensation of o-nitraniline with excess formaldehyde in ethanol/water, the methylene-bis(-o-nitraniline) obtained being then isolated. In the second stage, the isolated product is rearranged in the presence of concentrated hydrochloric acid to obtain the desired bis-(4-amino-3-nitrophenyl)-methane.

It has now been found that when the reaction is performed in water, in the presence of a sufficient amount of sulfuric acid, it surprisingly suffices, after condensation of the reaction mixture is completed, to allow the reaction to continue at an elevated temperature of about 100° C. so that the rearrangement resulting in the desired products in approximately quantitative yield is effected. Apart from the benefit of a single-stage reaction and the elimination of the complicated intermediate isolation step hitherto necessary, and also the benefit of a considerable increase in yield, the novel process of the present invention offers for example the following advantages: an excess of formaldehyde is not necessary and, by virtue of the replacement of hydrochloric acid with sulfuric acid, the risk of the formation of cancerogenic bis-chloromethyl ether is avoided.

The invention accordingly relates to a process for producing bis-(4-amino-3-nitrophenyl)-methane in one stage, which process comprises condensing 2 mols of o-nitraniline with 1 mol of formaldehyde firstly in water at a temperature of between 20° and 40° C. in the presence of sulfuric acid, and subsequently rearranging the formed methylene-bis-(o-nitraniline) by treatment of the reaction mixture at a temperature of between 90° and 100° C.

There are advantageously used, to 1 part of o-nitraniline 2-5 parts by weight of water and 1.5-2.5 parts by weight of concentrated (92-94%) sulfuric acid. To 1 part of of o-nitraniline are preferably used 3 to 4 parts by weight of water and 1.7 to 2.2 parts by weight of concentrated sulfuric acid.

The condensation of o-nitraniline with formaldehyde is preferably performed at a temperature of between 25° and 35° C., particularly between 28° and 30° C., and the subsequent rearrangement between 97° and 100° C.

The formaldehyde can be in the form of an aqueous solution, especially an approximately 30-37% aqueous solution, or in the form of paraformaldehyde. When paraformaldehyde is used, it is necessary to add the 5- to 20-fold amount, preferably the 8- to 12-fold amount, in weight, relative to the paraformaldehyde, of a depolymeriser, for example dimethylformamide, dimethylacetamide or dimethyl sulfoxide.

The condensation time is in general between 1½ and 3 hours; whilst about 3 to 5 hours are necessary for the rearrangement reaction.

The addition of 0.2 to 2% by weight, relative to the o-nitraniline, of an emulsifier at the commencement of the reaction is advisable. Suitable emulsifiers are for example: amines and amine salts, such as quaternary ammonium or pyridinium salts (especially mixtures of lauryltrimethyl- and myristyltrimethylammonium chloride), ethylene oxide adducts, naphthalenesulfonic acid-formaldehyde condensates or sulfonates.

The final product is isolated, using customary methods, by filtration, neutralisation (for example with sodium carbonate solution), washing out with warm water and drying. By virtue of the high degree of purity of the product obtained, no additional purification is required; the product can be used for example directly, also in the water-wet condition, for hydrogenation to the tetramine, with subsequent diazotisation and cyclisation to methylene-bis-benzotriazole, the most important product produced therefrom.

The product according to the invention is a compound which plays an important part in the synthesis of cyclic nitrogen compounds, which are used for example as corrosion inhibitors.

The following Example further illustrates the invention without limiting its scope.

EXAMPLE 861 g of water are placed into a 2.5 liter sulfonating flask provided with a "Halbanker" stirrer, reflux condenser, thermometer and 500 ml dropping funnel, and there are then introduced, with stirring, 278 g of ortho-nitraniline and 2 g of an 80% aqueous solution of an emulsifier of the formula

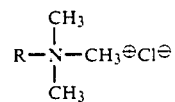

R = mixture of myristyl and lauryl.

An addition of 569 g of sulfuric acid is subsequently made via the dropping funnel within 5 minutes, in the course of which the temperature rises to about 70° C. The solution is cooled to 30° C., and to the suspension are then added 86 g of 35% aqueous formaldehyde solution. After two-hours' stirring at 28°-30° C., the temperature is raised within 45 minutes to 97°-100° C., and stirring is maintained at this temperature for 4 hours. Following the addition of 90 g of water and cooling to room temperature, the mixture is filtered through a suction filter. The filter residue is successively washed with 400 g of warm water, 400 g of a 5% sodium carbonate solution, and four times with portions each of 250 g of warm water. After drying at 90° C., there are thus obtained 280 g of 4,4'-diamino-3,3'-dinitrodiphenylmethane (=97% yield; content: 98%).

What is claimed is:

1. A process for producing bis-(4-amino-3-nitrophenyl)-methane in one stage, which process comprises
    condensing in a 2:1 molar ratio o-nitroaniline with formaldehyde firstly in water at a temperature of between 20° and 40° C. in the presence of sulfuric acid, wherein for each 1 part of o-nitroaniline, 3-4 parts by weight of water and 1.7-2.2 parts by weight of 92-94% sulfuric acid are present, and
    subsequently rearranging the formed methylene-bis-(o-nitroaniline) by heating of the reaction mixture at a temperature of between 90° and 100° C.

2. A process according to claim 1, wherein the condensation of o-nitraniline with formaldehyde is performed at a temperature of between 25° and 35° C., and the subsequent rearrangement between 97° and 100° C.

* * * * *